(12) United States Patent
Yu et al.

(10) Patent No.: US 10,150,936 B2
(45) Date of Patent: Dec. 11, 2018

(54) BRANCHED BIODEGRADABLE LOW FOAM NONIONIC SURFACTANTS

(71) Applicants: Dow Global Technologies LLC, Midland, MI (US); Rohm and Haas Company, Philadelphia, PA (US)

(72) Inventors: Wanglin Yu, Freeport, TX (US); Kara S. Weber, Freeport, TX (US); Jan E. Shulman, Collegeville, PA (US); John Hayes, Collegeville, PA (US)

(73) Assignees: Dow Global Technologies LLC, Midland, MI (US); Rohm and Haas Company, Philadelphia, PA (US)

(*) Notice: Subject to any disclaimer, the term of this patent is extended or adjusted under 35 U.S.C. 154(b) by 0 days.

(21) Appl. No.: 15/513,654

(22) PCT Filed: Sep. 17, 2015

(86) PCT No.: PCT/US2015/050549
§ 371 (c)(1),
(2) Date: Mar. 23, 2017

(87) PCT Pub. No.: WO2016/048764
PCT Pub. Date: Mar. 31, 2016

(65) Prior Publication Data
US 2017/0283742 A1 Oct. 5, 2017

Related U.S. Application Data

(60) Provisional application No. 62/054,402, filed on Sep. 24, 2014.

(51) Int. Cl.
| | | |
|---|---|---|
| C11D 1/722 | (2006.01) |
| C07C 43/11 | (2006.01) |
| C11D 1/72 | (2006.01) |
| C08G 65/26 | (2006.01) |
| C07C 43/10 | (2006.01) |
| C11D 3/00 | (2006.01) |

(52) U.S. Cl.
CPC .............. *C11D 1/722* (2013.01); *C07C 43/10* (2013.01); *C08G 65/2609* (2013.01); *C11D 1/72* (2013.01); *C11D 3/0026* (2013.01)

(58) Field of Classification Search
CPC ........ C11D 1/722; C11D 3/3707; C07C 43/11
See application file for complete search history.

(56) References Cited

U.S. PATENT DOCUMENTS

| | | | |
|---|---|---|---|
| 3,955,401 A | 5/1976 | Catherall | |
| 3,956,401 A | 5/1976 | Scardera et al. | |
| 4,317,940 A | 3/1982 | Scardera et al. | |
| 4,438,014 A * | 3/1984 | Scott ................... | C11D 3/0026 134/25.2 |
| 4,925,587 A | 5/1990 | Schenker et al. | |
| 5,425,894 A | 6/1995 | Welch et al. | |
| 5,612,305 A * | 3/1997 | Lewis ................... | C11D 1/825 510/220 |

FOREIGN PATENT DOCUMENTS

GB 2204321 11/1988

OTHER PUBLICATIONS

International Search Report & Written Opinion for related PCT Application PCT/US2015/050549, dated Mar. 11, 2016 (12 pgs).

* cited by examiner

*Primary Examiner* — Brian P Mruk
(74) *Attorney, Agent, or Firm* — Brooks, Cameron & Huebsch, PLLC

(57) ABSTRACT

A surfactant of structure (I) is useful as a biodegradable low foaming surfactant: where m is a value in a range of 3 to 10, n is a value in a range of 5 to 20 and z is a value in a range of 10 to 25.

(I)

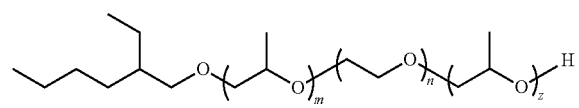

6 Claims, No Drawings

BRANCHED BIODEGRADABLE LOW FOAM NONIONIC SURFACTANTS

This application is a National Stage Application under 35 U.S.C. § 371 of International Application Number PCT/US2015/050549, filed Sep. 17, 2015 and published as WO 2016/048764 on Mar. 31, 2016, which claims the benefit to U.S. Provisional Application 62/054,402, filed Sep. 24, 2014, the entire contents of which are incorporated herein by reference in its entirety.

BACKGROUND OF THE INVENTION

Field of the Invention

The present invention relates to a nonionic surfactant that is a polypropylene oxide/polyethylene oxide/polypropylene oxide triblock polymer.

Introduction

Low foaming non-ionic surfactants are desirable in detergent and rinse aid products useful as hard surface cleaners, including for use in automatic dishwashers such as household dishwashers. Biodegradable low foaming non-ionic surfactant are particularly desirable in order to avoid long-term impact on the environment. Examples of low foaming biodegradable non-ionic surfactants are known, but they have some technical limitations in order to achieve biodegradability.

U.S. Pat. No. 55,662B1 discloses polypropylene oxide (PO)-polyethylene oxide (EO) diblock copolymers that are reportedly biodegradable. The diblock copolymer is initiated with a linear initiator so as to have a linear aliphatic hydrocarbon on the PO end of the molecule.

U.S. Pat. No. 4,925,587 also discloses a diblock copolymer with a linear aliphatic hydrocarbon end.

U.S. Pat. No. 3,955,401 and U.S. Pat. No. 4,317,940 each describe a PO-EO-PO triblock copolymer prepared with a linear initiator so to have a linear aliphatic hydrocarbon on a PO end of the copolymer.

Notably, each of the surfactants in these references expressly is initiated with a linear initiator in order to achieve a linear hydrocarbon group on the final surfactant. The reason a linear hydrocarbon group is so important is because it has long been known that branching in a surfactant determinately affects the biodegradability of the surfactant. For example, U.S. Pat. No. 3,955,401 and U.S. Pat. No. 4,317,940 each teach that "the biodegradability of the product is detrimentally affected by branching." Therefore, to achieve biodegradability, the surfactants are prepared using linear alcohols as initiators. The detrimental effect of branching in biodegradability is further affirmer in a study of ethoxylate polymers that concluded that polymers initiated with single or multiple-branched alcohols did not show a significant degradation while significant degradation was observed to ethoxylates with linear alcohols and iso-alcohol. (See, M. T. Muller, M. Siegfried and Urs Bauman; "Anaerobic Degradation and Toxicity of Alcohol Ethoxylates in Anaerobic Screening Test Systems", presented at $4^{th}$ World Surfactants Congress, 1996).

It would be unexpected in the art to discover a biodegradable low foaming non-ionic surfactant that has a branched alkyl end group.

BRIEF SUMMARY OF THE INVENTION

The present invention provides an unexpected biodegradable low foaming non-ionic surfactant that has a branched alkyl end group. Contrary to common understanding, the surfactant is readily biodegradable despite having a branched alkyl end group. The branched alkyl end group surprisingly can have two or more carbons on each branch so branches are more than methyl groups.

As part of discovering the present invention, it was discovered that the non-ionic surfactant necessarily was an alkyl PO/EO/PO triblock in order to achieve biodegradability. Similar PO/EO diblock non-ionic polymers do not demonstrate acceptable biodegradability.

In a first aspect, the present invention is a surfactant having the following structure (I):

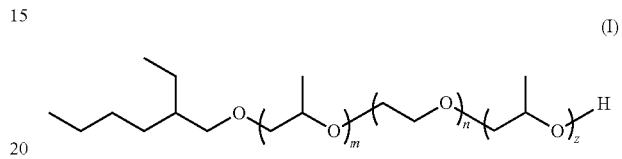

where m is a value in a range of 3 to 10, n is a value in a range of 5 to 20 and z is a value in a range of 5 to 30.

In a second aspect, the present invention is a method of using the surfactant of any previous claim, the method comprising placing a detergent composition containing the surfactant in an automatic dishwasher, such as for example an automatic household dishwasher.

The present invention is useful as a low foaming non-ionic surfactant for applications such as cleaning solutions.

DETAILED DESCRIPTION OF THE INVENTION

"And/or" means "and, or alternatively". All ranges include endpoints unless otherwise stated. Parts per million (ppm) refers to weight parts based on total aqueous solution weight unless otherwise indicated. Subscript values in polymer formulae refer to mole average values for the designated component of the polymer.

Test methods refer to the most recent test method as of the priority date of this document unless a date is indicated with the test method number as a hyphenated two digit number. References to test methods contain both a reference to the testing society and the test method number. Test method organizations are referenced by one of the following abbreviations: ASTM refers to ASTM International (formerly known as American Society for Testing and Materials); EN refers to European Norm; DIN refers to Deutsches Institut für Normung; and ISO refers to International Organization for Standards.

The surfactant of the present invention has the following structure (I):

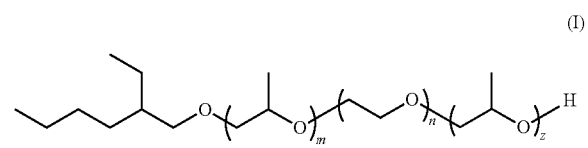

where:

m is a value of 3 or more, preferably 4 or more, more preferably 5 or more and can be 6 or more while at the same time is 10 or less, preferably 9 or less, more preferably 8 or less, even more preferably 7 or less, yet even more preferably 6 or less and most preferably 5 or less. Most desirably, m is 5.

n is a value of 5 or more, preferably 7 or more, more preferably 9 or more and at the same time is 30 or less, preferably 25 or less, more preferably 20 or less, yet more preferably 15 or less, yet even more preferably 10 or less, and can be 9 or less and even 7 or less.

z is a value of 5 or more, preferably 10 or more and at the same time is 30 or less, preferably 25 or less. It is important for the value of z to be non-zero in order to achieve biodegradability. As the data in the Examples section below reveals, if z is zero the resulting surfactant does not demonstrate acceptable biodegradability. Hence, z must be non-zero for the surfactant to achieve biodegradability. This is one of the unexpected discoveries of the present invention.

The ratio of n to z (that is the value of n/z) is desirably one or less than one in order to achieve optimal defoaming performance.

The surfactant has a 2-ethylhexyl (2EH) moiety on one end and a hydroxyl moiety on the other end. The 2EH moiety is a branched alkyl with each branch having a length of two carbons or more. The 2EH end group moiety can be introduced into the molecule by using 2-ethylhexanol as an initiator to polymerize the blocks of propylene oxide (PO) and ethylene oxide (EO). Despite having a branched alkyl end group, the present surfactant is biodegradable. This is an unexpected result based on prior art teachings that explain having a branched alkyl detrimentally affects biodegradability. Surprisingly, the present surfactant having a branched alkyl end group was found to be biodegradable when in a PO/EO/PO triblock structure. It also found to be particularly good at defoaming.

The surfactant of the present invention is useful as a component in a fully formulated detergent in hard surface cleaning formulations, such as dishwashing detergents for automatic dishwashers. To use the surfactant of the present invention as a dishwasher detergent, place the detergent composition containing the surfactant into an automatic dishwasher.

The following examples further illustrate aspects of the present invention.

EXAMPLES

Prepare seven different surfactants of structure (I) as described in Table 1 using the following procedure.

Charge 780.0 grams of 2-ethylhexanol and 10.81 grams of 85% potassium hydroxide pellets into a nine liter reactor that has been purged with nitrogen. Gradually apply vacuum to the reactor over two hours to achieve 100 millimeter mercury. Remove 15.8 grams of mixture from the reactor and measure for water content by Karl Fisher titration (411 parts per million by weight (ppm)). Pressurize and vent the reactor seven times with dry nitrogen to remove atmospheric oxygen and pressurize with nitrogen to 110 to 139 kiloPascals (kPa) at 25° C. Heat the contents of the reactor while agitating to 130° C. and then meter in 1660 grams propylene oxide over 4 hours. After completing the propylene oxide feed, agitate the reactor contents at 130° C. for an additional 2 hours and then cool to 60° C. Remove 142.9 grams of reactor contents. Heat the reactor contents to 130° C. and meter in 2070 grams of ethylene oxide into the reactor over 4 hours. After completing the ethylene oxide feed, agitate the reactor contents at 130° C. for 2 hours and then cool to 60° C. Remove 142.9 grams of the reactor contents. Heat the reactor contents to 130° C. and meter in 1475 grams of propylene oxide over 4 hours and then continue agitating at 130° C. for an additional 2 hours. Cool the reactor contents to 60° C.

Remove 158.2 grams of the reactor contents and neutralize with acetic acid to achieve a pH of 4-8 (in 10% aqueous solution) to obtain Example (Ex) 1 Surfactant.

Heat the reactor contents back to 130° C. and meter in 1170 g of propylene oxide into the reactor over 4 hours. Continue agitating at 130° C. for an additional 2 hours and then cool to 60° C. Remove 118.7 grams of reactor contents and neutralize with acetic acid in an 10% aqueous solution to a pH of 4-8 to obtain Ex 2 Surfactant.

Heat the reactor contents back to 130° C. and meter in 970 grams of propylene oxide over 4 hours and then continue to agitate for an additional 2 hours at 130° C. Cool the reactor contents to 60° C. Neutralize the contents of the reactor with acetic acid in a 10% aqueous solution to achieve a pH of 4-8 to obtain Ex 3 Surfactant.

Prepare surfactant Exs 4-7 in like manner adjusting the amount of PO and EO feeds to the appropriate mole ratios for those particular surfactants.

The properties of each surfactant are included in Table 1. Each surfactant has the structure of structure (I) and the structure of each is given by specifying the values for m, n and z for each surfactant.

Determine cloud point with a one weight-percent (wt %) solution of surfactant in deionized water using a Mettler Toledo FP900 ThermalSystem with an FP90 central processor and FP81 measuring cell according to ASTM D2024-09.

Determine Draves Wetting values according to ASTM D2281-69. The results are reported as the minimum concentration (in wt %) required to wet the tested skein in 20 seconds. Lower values correspond to better wetting ability for a surfactant.

Determine contact angle at 21-23° C. using a Kruss DSA-100 Drop Shape Analyzer with a movable sample stage and Kruss software DSA3.exe to control operation of the instrument and perform data analysis. Perform contact angle measurement on a static sessile drop on a parafilm substrate. Place parafilm on a glass microscope slide using a small amount of adhesive on each edge of the slide to hold the film in place. Place the substrate on a sample stage and five liquid drops of a 0.1 wt % solution of surfactant in deionized water are deposited on the substrate programmatically using the procedure predefined via DSA software. Drop volume is five microliters. Rate of drop deposition is six microliters per minute and drop measurements are made immediately after drop placement. Once a drop is place an image of the drop is collected, the baseline is determined, left and right contact angles are determined by software and the arithmetic mean of left and right contact angles is calculated for each drop. The result is reported as a mean of eth values from three groups of five drops (mean of 15 total drops).

Determine surface tension of a surfactant using a 0.1 wt % aqueous surfactant solution and a Kruss D12 tensiometer fitted with a Wilhelmy platinum plate at 25° C. Solutions are made by dissolving surfactant into deionized water. The deionized water used to make the solutions is 72-73 milliNewtons per meter. Results are reported as a mean of five repeated testing values with the standard deviation being less than 0.1 mN/m.

Determine biodegradability (Biodeg) according to Organization for economic co-operation and development (OECD) test method 301F. Determine Aquatic toxicity (A-tox) milligrams per liter (mg/L) according to OECD Guidelines for the Testing of Chemicals, "Daphnia sp., Acute Immobilization Test", Test Guideline 202, adopted 13 Apr. 2004.

TABLE 1

| Ex | Structure (m, n, z) | Cloud Point (° C.) | Draves wetting 20 s wetting conc'n (wt %) | contact angle (degrees) | surface tension (dynes/cm) | Biodegradability (%) | A-tox EC50 at 48 hours (mg/L) |
|---|---|---|---|---|---|---|---|
| 1 | 5, 9, 5   | 42 | 0.12 | 63 | 34 | 85 | >100 |
| 2 | 5, 9, 10  | 31 | 0.13 | 68 | 34 | NM* | NM* |
| 3 | 5, 9, 15  | 24 | 0.13 | 69 | 35 | 90 | 65.6 |
| 4 | 5, 15, 10 | 41 | 0.22 | 70 | 34 | 80 | >100 |
| 5 | 5, 15, 15 | 32 | 0.18 | 72 | 35 | NM* | NM* |
| 6 | 5, 15, 20 | 27 | 0.17 | 73 | 35 | 88 | 50.6 |
| 7 | 5, 15, 25 | 22 | 0.15 | 72 | 35 | NM* | NM* |

*NM mean not measured. However for examples where only z is changing, the NM value for biodegradability and toxicity is expected to fall between values for the analogous surfactants with higher and lower z values.

Biodegradability

Each of the surfactants demonstrate a biodegradability value that is 80% or higher. A value of 60% is deemed "readily biodegradable" under the test method. Therefore, each of the surfactants is deemed readily biodegradable.

In contrast, the biodegradability of similar 2EH-PO-EO diblock materials have biodegradability results that are significantly lower. For example 2EH(PO)$_{4.5}$(EO)$_8$ exhibits a biodegradability of 61%—barely passing as readily biodegradable. 2EH(PO)$_9$(EO)$_9$ demonstrate biodegradability of 53% and 2EH(PO)$_4$(EO)$_{10}$ is also less than 60%, neither of which pass as being readily biodegradable.

Foaming

Determine the defoaming performance of the surfactants in the following Milk Soil Defoaming test. Prepare an aqueous solution of each surfactant at a loading of 0.01 wt % surfactant based on solution weight. To 186 milliliters (mL) of the solution add 0.6 grams sodium hydroxide. Then, with the resulting solution in one-liter container of a Waring™ Laboratory Blender (Model 31DM33, from Waring Commercial), add 15 mL of milk dispersion (10 wt % milk powder in water). Turn on the blender at high speed for 60 seconds. Stop the blender and record foam height at 0, 15, 30, 60 and 120 seconds.

Conduct the test for the 7 example surfactants, a blank that contains no surfactant and three reference solutions that contain commercial surfactants that are all known as effective protein soil foam control agents: TRITON™ CF-32 nonionic defoamer (TRITON is a trademark of The Dow Chemical Company), PLURAFAC™ SLF-180 low foaming alcohol alkoxylate and PLURAFAC™ SLF-18 low foaming alcohol alkoxylate (PLURAFAC is a trademark of BASF).

Table 2 contains the foam height values in millimeters for each of the solutions.

TABLE 2

| | Foam Height (mm) | | | | |
|---|---|---|---|---|---|
| Example | 0 seconds | 15 seconds | 30 seconds | 60 seconds | 120 seconds |
| Blank | 40 | 30 | 29 | 27 | 23 |
| 1 | 26 | 27 | 14 | 6 | 3 |
| 2 | 22 | 12 | 8 | 5 | 2 |
| 3 | 17 | 7 | 4 | 3 | 1 |
| 4 | 23 | 17 | 10 | 2 | 0 |
| 5 | 22 | 12 | 4 | 1 | 0 |

TABLE 2-continued

| | Foam Height (mm) | | | | |
|---|---|---|---|---|---|
| Example | 0 seconds | 15 seconds | 30 seconds | 60 seconds | 120 seconds |
| 6 | 16 | 5 | 2 | 1 | 0 |
| 7 | 7 | 3 | 1 | 0 | 0 |
| Triton CF-32 | 24 | 19 | 6 | 0 | 0 |
| Plarafac SLF-180 | 20 | 12 | 6 | 4 | 2 |
| Plarafac SLF-18 | 19 | 11 | 5 | 4 | 2 |

The data in Table 2 reveals that all of the samples have similar or better defoaming performance relative to the commercial materials and an initial foam height of less than 30 millimeters.

Automatic Dishwashing Performance

Characterize the detergency of the surfactants in an automatic dishwasher according to the ASTM 3566-85 test method under North American test conditions. Use a Sears Kenmore model 665.13.04 Series 2K113 dishwasher with water preheated to 55° C. in a short wash cycle program. Use four Libbey-Collin glasses (Model #53) for scaling and spotting characterization. Place the glasses facing downward in the upper rack of the dishwater in different corners of the dishwasher. Include in a dishwasher an additional load of consumer relevant dishwashing items including clean porcelain, ceramic, melamine and glass plates and/or cups, stainless steel cutlery and plastic tumblers.

Before conducting the study, subject the dishwasher and ballast load to a 3-cycle automatic dishwasher machine strip (two washes at 55° C. and one wash at 60° C.) followed by 2-cycle glassware strip. The initial automatic dishwasher machine strip utilizes a commercial North American dishwashing detergent (CASCADE Complete dishwasher soap; CASCADE is a trademark of Procter & Gamble) using the one hour short cycle automatic dish program at 55° C. The follow that up with a separate citric acid wash. For the citric acid wash fill the main cup with citric acid (approximately 35 grams) and close the cup. Also add approximately 15-20 grams of citric into the dishwasher basin at the very start of the pre-wash cycle. The third automatic dishwasher machine strip is a sanitation machine strip at 60° C. utilizing a predetermined normal wash dishwashing program with sanitation rinse. Then, add the glasses to the automatic dishwasher and conduct two consecutive strip cycles at 55° C. on the one hour short cycle automatic dish program.

For the actual test, use water specifically prepared to a 300 parts per million by weight hardness (2:1 Ca:Mg) by adding 100,000 ppm of a 2:1 Ca:Mg ion stock solution to tap water. Confirm hardness values by titrating with an ethylenediaminetetraacetic acid (EDTA) stock solution and indicator, then titrate until a distinct color change is noted.

Characterize performance using a detergent formulation as set forth in Table 3, where 29 weight-percent (wt %) of sodium sulfate and 0 wt % surfactant is used in a baseline "detergent" and 27 wt % sodium sulfate and 2 wt % surfactant is used to characterize performance of each surfactant. In addition to each of surfactants of Exs 1-7, a detergent using DOWFAX™ 20B102 linear alcohol alkoxylate as a reference detergent commonly used in automatic dishwashers. DOWFAX is a trademark of The Dow Chemical Company. A second reference is also explored using PLURAFAC™ SLF-180 Low Foaming alcohol alkoxylate. PLURAFAC is a trademark of BASF Wyandotte Corporation.

TABLE 3

| Component | wt % of Formulation |
|---|---|
| Sodium citrate | 15.0 |
| Sodium Carbonate | 20.0 |
| Sodium Bicarbonate | 10.0 |
| Sodium Disilicate (Britesil ™ H2O) | 5.0 |
| Sodium Percarbonate | 15.0 |
| Acrylic homopolymer (Acusol ™ 445NG granulated detergent polymer) | 2.0 |
| Acrylic/sulfonate copolymer (Acusol ™ 588G (granulated) dispersant polymer) | 4.0 |
| Sodium Sulfate | 27.0 (surfactant test)/ 29.0 (baseline) |
| Surfactant | 2.0 (surfactant test)/ 0.00 (baseline) |

Britesil is a trademark of PQ Corporation
Acusol is a trademark of The Dow Chemical Company Prepare a ballast soil by melting four sticks of margarine (approximately 400 grams) on a hotplate/stirrer, add approximately 90 grams non-fat dry milk while mixing with an overhead mixer slowly for 15-30 minutes. Remove the mixture from the heat source and allow to cool to about 25° C. while slowly mixing. Once cooled to about 25° C., place the ballast soil (or "food soil") in a refrigerator/freezer until solid.

Evaluation runs are done using by placing pieces of porcelain, plastic and cutlery evenly in the lower and upper basket of the dish washing machine. Distribute the Libbey-Collin glasses evenly in the upper rack. Weight out 40 grams of "frozen" ballast soil into a beaker and then distribute soil on the dishwasher door and place the remaining ballast soil in the lower rack of the dishwasher. Select the "short wash" dishwashing cycle (approximately one hour).

Run the dishwasher for 5 cycles, each time adding a 20 gram dosage of the detergent formulation being tested and introducing another 40 grams of frozen ballast as described. Remove one Libbey-Collin glass after cycles 1, 2, 3 and 5 and evaluate its cleanliness.

Determine glass cleanliness using the rating system shown in Table 4. Evaluations of the glasses takes place the morning after glasses have been removed from the washer in order to allow them to cool and equilibrate to the ambient temperature. Evaluations are done in a light chamber (box) that illuminates the glasses.

TABLE 4

| Rating | Spotting Character | Filming Character |
|---|---|---|
| 1 | None | None |
| 2 | Random Spots | Barely Perceptible |
| 3 | About ¼ of surface covered | Slight |
| 4 | About ½ surface covered | Moderate |
| 5 | virtually completely covered | Heavy |

Using two different people doing evaluations, average the scores of the evaluators to assign a value for each detergent formulation.

Table 5 contains the results for the Spotting Character evaluation for the baseline formulation, reference detergent and detergents containing each of the surfactants. Ratings are an average of ratings by two reviewers.

Table 6 contains results for the Filming Character evaluation for the baseline formulation, reference detergent and detergents containing each of the surfactants. Ratings are an average of ratings by two reviewers.

TABLE 5

| | Spotting Character Rating | | | |
|---|---|---|---|---|
| Surfactant in Formulation | Cycle 1 | Cycle 2 | Cycle 3 | Cycle 5 |
| None (base line) | 4.3 | 4.5 | 4.8 | 5.0 |
| DOWFAX ™ 20B102 linear alcohol alkoxylate | 3.0 | 2.2 | 2.0 | 2.0 |
| PLURAFAC ™ low forming alcohol alkoxylate | 1.8 | 2.0 | 2.0 | 2.0 |
| Ex 1 | 3.6 | 4.3 | 4.7 | 5.0 |
| Ex 2 | 1.7 | 2.1 | 2.3 | 2.2 |
| Ex 3 | 2.4 | 2.4 | 3.0 | 3.0 |
| Ex 4 | 2.0 | 2.2 | 2.4 | 2.2 |
| Ex 5 | 2.0 | 2.2 | 2.0 | 2.2 |
| Ex 6 | 1.8 | 2.0 | 2.0 | 2.0 |
| Ex 7 | 2.0 | 2.7 | 3.0 | 3.0 |

TABLE 6

| | Filming Character Rating | | | |
|---|---|---|---|---|
| Surfactant in Formulation | Cycle 1 | Cycle 2 | Cycle 3 | Cycle 5 |
| None (base line) | 2.7 | 3.3 | 4.0 | 5.0 |
| DOWFAX ™ 20B102 linear alcohol alkoxylate | 2.0 | 2.2 | 2.4 | 2.9 |
| PLURAFAC ™ low forming alcohol alkoxylate | 1.8 | 2.2 | 2.6 | 3.2 |
| Ex 1 | 2.6 | 2.9 | 3.5 | 4.0 |
| Ex 2 | 1.9 | 2.1 | 2.2 | 2.5 |
| Ex 3 | 1.9 | 2.1 | 2.2 | 2.7 |
| Ex 4 | 2.5 | 3.3 | 4.0 | 5.0 |
| Ex 5 | 2.2 | 2.4 | 2.8 | 3.3 |
| Ex 6 | 1.8 | 2.3 | 2.5 | 2.8 |
| Ex 7 | 2.4 | 2.7 | 2.8 | 3.0 |

The data in Tables 5 and 6 reveal that each of Exs 1-7 show some effectiveness as low foam surfactants in automatic dishwashing applications. The best performing surfactants rival if not outperform the commercial reference surfactants for use in automatic dishwasher detergents.

The invention claimed is:

1. A surfactant having the following structure (I):

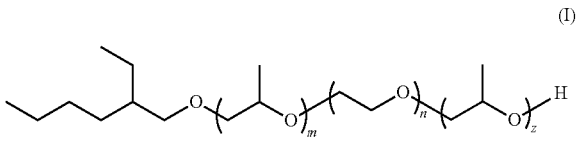

(I)

where m is a value in a range of 3 to 10, n is a value in a range of 5 to 20 and z is a value in a range of 5 to 30.

2. The surfactant of claim 1, further characterized by m being 5, n being in a range of 9 to 15 and z being in a range of 5 to 25.

3. The surfactant of claim 1, further characterize by the ratio of n to z being one or less.

4. The surfactant of claim 1, further characterized by m being 5, n being a value in a range of 5 to 9 and z being a value in a range of 10 to 25.

5. A method of using the surfactant of any previous claim, the method comprising placing a detergent composition containing the surfactant in an automatic dishwasher.

6. The surfactant of claim 1, further characterized by m being 5, n being a value in a range of 10 to 15 and z being a value in a range of 10 to 25.

* * * * *